United States Patent [19]

Baldwin

[11] Patent Number: 4,774,243

[45] Date of Patent: Sep. 27, 1988

[54] DOPAMINE AGONISTS FOR TREATING ELEVATED INTRAOCULAR PRESSURE

[75] Inventor: John J. Baldwin, Gwynedd Valley, Pa.

[73] Assignee: Merck & Co., Inc., Rahway, N.J.

[21] Appl. No.: 813,323

[22] Filed: Dec. 24, 1985

[51] Int. Cl.$^4$ .......................................... A61K 31/535
[52] U.S. Cl. .............................. 514/229.5; 514/227; 514/913
[58] Field of Search ................... 514/239, 227, 913

[56] References Cited

U.S. PATENT DOCUMENTS

| | | | |
|---|---|---|---|
| 4,238,486 | 12/1980 | Jones | 514/239 |
| 4,349,548 | 9/1982 | Jones | 514/239 |
| 4,420,480 | 12/1983 | Jones | 514/239 |
| 4,493,836 | 1/1985 | Nedelec et al. | 514/239 |
| 4,503,053 | 3/1985 | Nedelec et al. | 514/239 |

FOREIGN PATENT DOCUMENTS 0080115  6/1983  European Pat. Off. ............ 514/227

OTHER PUBLICATIONS

Mekki et al., *The Lancet*, 1250, (1983).
Potter et al., *Cur. Eye. Res.*, 2, 281, (1983).
Macri et al., *Exp. Eye Res., 26, 85, (1978)*.
Green et al., *Exp. Eye Res.*, 29, 423, (1979).
Potter et al., *Cur. Eye Res.*, 3, 851, (1984).
Shannon et al., *Ophthalmol.*, 15, 371, (1976).

*Primary Examiner*—Douglas W. Robinson
*Attorney, Agent, or Firm*—William H. Nicholson; Michael C. Sudol, Jr.

[57] ABSTRACT

Topical ocular administration of a dopamine agonist is effective in lowering abnormally elevated intraocular pressure and is useful in the prevention and treatment of glaucoma and related ocular diseases.

7 Claims, No Drawings

DOPAMINE AGONISTS FOR TREATING ELEVATED INTRAOCULAR PRESSURE

SUMMARY OF THE INVENTION

This invention is concerned with the use of dopamine agonists in the treatment of abnormally elevated intraocular pressure, especially in the prevention and treatment of pathological damage such as in glaucoma.

In particular the invention is concerned with the use of the compounds of structural formula:

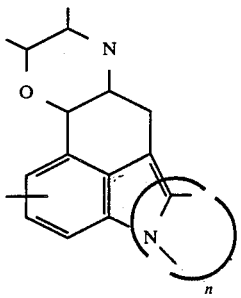

or an ophthalmologically acceptable salt thereof wherein n is o or 1.

BACKGROUND OF THE INVENTION

Glaucoma is an ocular disorder associated with elevated ocular pressures which are too high for normal ocular activity and may reuslt in irreversible loss of visual function. If untreated, glaucoma may eventually lead to blindness. Ocular hypertension. i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma are guite unsatisfactory such as pilocarpine and physostigmine. β-Adrenergic blocking agents are distintly better but still present cardiovascular and pulmonary adverse reactions. Carbonic anhydrase inhibitors are used to treat elevated intraocular pressure by systemic adminstration but only as a last resort because of the potential for numerous adverse reactions. Although there are topically active carbonic anhydrase inhibitors on the horizon, none has yet become available to the ophthalmologist for the control of elevated intraoculor pressure.

Now, with the present invention, there is provided a novel means of controlling abnormally elevated intraocular pressure by the topical ocular administration of a dopamine agonist.

DETAILED DESCRIPTION OF THE INVENTION

The novel method of treatment of this invention comprises the topical ocular administration to a patient in need of such treatment of an effective intraocular pressure lowering amount of a dopamine agonist.

The dopamine agonists of particular interest in the novel method of this invention are discribed in U.S. Pat. Nos. 4,238,486 and 4,420,480 the disclosures of which are incorporated herein by reference and have the structural formulae I and II respectively:

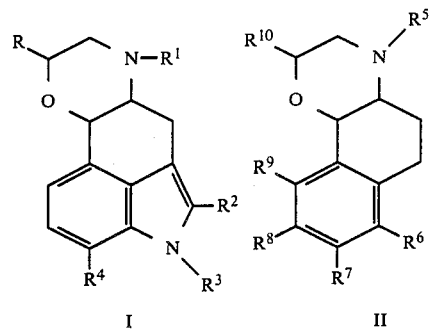

or an ophthalmologically acceptable salts thereof wherein:

R is
 (1) hydrogen,
 (2) $C_{1-6}$alkyl, or
 (3) phenyl;

$R^1$ is
 (1) hydrogen,
 (2) $C_{1-4}$alkyl,
 (3) $C_{3-6}$cycloalkyl,
 (4) $C_{3-6}$cycloalkyl-$C_{1-4}$alkyl,
 (5) $C_{3-4}$alkenyl,
 (6) phenyl-$C_{1-4}$alkyl;

$R^2$ is
 (1) hydrogen,
 (2) $C_{1-3}$alkyl,
 (3) chloro, or
 (4) bromo;

$R^3$ is
 (1) hydrogen,
 (2) $C_{1-3}$alkyl, or
 (3) phenyl-$C_{1-4}$alkyl;

$R^4$ is
 (1) hydrogen,
 (2) chloro,
 (3) bromo,
 (4) $C_{1-4}$alkoxy,
 (5) hydroxy, or
 (6) $C_{1-6}$alkyl;

$R^5$ is
 (1) hydrogen,
 (2) $C_{1-4}$alkyl,
 (3) $C_{2-5}$alkenyl, or
 (4) phenyl-$C_{1-4}$alkyl;

$R^6$, $R^7$, $R^8$, and $R^9$ are independently
 (1) hydrogen,
 (2) $C_{1-3}$alkoxy,
 (3) hydroxy,
 (4) $C_{1-4}$alkyl,
 (5) halo, such as fluoro, chloro or bromo,
 (6) phenyl-$C_{1-3}$alkoxy, or
 (7) adjacent R groups taken together are methylenedioxy; and $R^{10}$ is hydrogen, $C_{1-3}$alkyl or phenyl.

In compound I it is preferred that $R^1$ is $C_{1-4}$alkyl, especially ethyl, and that $R^3$ is hydrogen. It is even more preferred that $R^2$, $R^3$ and $R^4$ all be hydrogen. A preferred species is trans-4, 6, 6a, 8, 9, 10a-hexahydro-7-ethyl-7H-indolo[3,4:g,h] [1,4]-benzoaxine.

In compound II it is preferred that $R^5$ is $C_{1-4}$alkyl, especially ethyl or n-propyl, and one or more of $R^6$, $R^7$, and $R^9$ are hydroxy, methoxy, acetoxy or pivaloyloxy, especially wherein $R^9$ is hydroxy, methoxy, acetoxy or pivaloyloxy. A preferred species is trans-1a, 2, 3, 4a, 5, 6-hexahydro-9-hydroxy-4-n-propyl-4H-naphth[1,2-b]-1,4-oxazine.

An effective intraocular pressure lowering amount of the dopamine agonist, applied topically, comprises about 0.5 µg to 250 µg preferably about 5 µg to 100 µg per eye on a one to three times a day regimen.

The pharmaceutical preparation which contains the active compound conveniently may be admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethylcellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenylethanol, buffering ingredients such as sodium chloride, sodium borate, sodium acetate, gluconate buffers, and other conventional ingredients sucb as sorbitan monolaurate, triethanolamine oleate, polyoxyethylene sorbitan monopalmitate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles, aqueous gel vehicles and the like. Generally, the drug is present in such vehicles in an amount of from 0.01 to about 2% by weight or more. Preferably the drug is present in an amount of from about 0.05 to 1% by weight.

While many patients find liquid medication to be entirely satisfactory, others may prefer a solid medicament that is topically applied to the eye, for example, a solid dosage form that is suitable for insertion into the cul-de-sac. To this end the dopamine agonist can be included with a non-bioerodible insert, i.e. one which after dispensing the drug remains essentially intact, or a bioerodible insert, i.e. one that either is soluble in lacrimal fluids, or otherwise disintegrates. While the insert employed is not critical, those disclosed in U.S. Pat. Nos. 3,630,200 Higuchi; 3,811,444 Heller et al.; 4,177,256 Michaels et al.; 3,868,445 Ryde et al.; 3,845,201 Haddad; 3,981,303 Higuchi; and 3,867,519 Michaels, are satisfactory; in general, however, the insert described below is found preferable.

For example, one may use a solid water soluble polymer as the carrier for the medicament. The polymer used to form the insert may be any water soluble non-toxic polymer, for example, cellulose derivatives such as methylcellulose, sodium carboxymethyl cellulose, or a hydroxy lower alkyl cellulose such as hydroxyethyl cellulose, hydroxypropyl cellulose, hydroxypropylmethyl cellulose and the like; acrylates such as polyacrylic acid salts, ethyl acrylates, polyacrylamides; natural products such as gelatin, alginates, pectins, tragacanth, karaya, chondrus, agar, acacia; the starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, and mixtures of said polymer.

The following examples of ophthalmic formulations are given by way of illustration.

EXAMPLE 1

Solution Composition

| | a |
|---|---|
| trans-4, 6, 6a, 8, 9, 10a-hexahydro-7-ethyl-7H—indolo-[3,4-g,h][1,4]benzoxazine | 100 mg. |
| Monobasic sodium phosphate .2H$_2$O | 9.38 mg. |
| Dibasic sodium phosphate .12H$_2$O | 28.48 mg. |
| Benzalkonium chloride | 0.10 mg. |
| Water for injection q.s. ad. | 10 ml. |

The compound, phosphate buffer salts, and benzalkonium chloride are added to and admixed with water. The pH of the resulting admixture is adjusted to 6.8 and the final formulation diluted to volume. The formulation is rendered sterile by appropriate means, such as starting the preparative procedure with sterile components and proceeding under sterile conditions, irradiating or autoclaving the finished formulation, or the like.

EXAMPLE 2

| Trans-1a, 2, 3, 4a, 5, 6-hexahydro-9-hydroxy-4-n-propyl-4H—naphth[1,2-b]-1,4-oxazine hydrochloride | 5 mg. |
|---|---|
| petrolatum q.s. ad. | 1 gram |

The compound and the petrolatum are aseptically combined.

EXAMPLE 3

| trans-4, 6, 6a, 8, 9, 10a-hexahydro-7-ethyl-7H—indolo-[3,4-g,h][1,4]benzoxazine | 0.1 mg |
|---|---|
| Hydroxypropylcellulose q.s. | 10 mg. |

Ophthalmic inserts are manufactured from compression molded films which are prepared on a Carver Press by subjecting the powdered mixture of the above ingredients to a compressional force of 12,000 lbs. (gauge) at 300° F. for one to four minutes. The film is cooled under pressure by having cold water circulate in the platen. Ophthalmic inserts are then individually cut from the film with a rod-shaped punch. Each insert is placed into a vial, which is then placed in a humidity cabinet (88% R.H. at 30° C.) for two to four days. After removal from the humidity cabinet, the vials are stoppered and then capped. The vials containing the hydrate insert are then autoclaved at 250° F. for ½ hour.

EXAMPLE 4

| Trans-1a, 2, 3, 4a, 5, 6-hexahydro-9-hydroxy-4-n-propyl-4H—naphth[1,2-b]-1,4-oxazine hydrochloride | 0.1 mg. |
|---|---|
| Hydroxypropyl cellulose q.s. ad. | 10 mg. |

Ophthalmic inserts are manufactured from a solvent cast film prepared by making a viscous solution of the powdered ingredients listed above using methanol as the solvent. The solution is placed on a Teflon plate and allowed to dry at ambient conditions. After drying, the film is placed in an 88% R. H. cabinet until it is pliable. Appropriately sized inserts are cut from the film.

EXAMPLE 5

| | |
|---|---|
| trans-4, 6, 6a, 8, 9, 10a-hexahydro-7-ethyl-7H—indolo-[3,4-g,h][1,4]benzoxazine | 0.1 mg. |
| Hydroxypropylmethyl cellulose q.s. ad. | 10 mg. |

Ophthalmic inserts are manufactured from a solvent cast film which is prepared by making a viscous solution of the powdered blend of the above ingredients using a methanol/water solvent system (10 ml. methanol is added to 2.5 g. of the powdered blend, to which 11 ml. of water (in three divided portions) is added. The solution is placed on a Teflon plate and allowed to dry at ambient conditions. After drying, the film is placed in an 88% R. H. cabinet until it is pliable. Appropriately sized inserts are then cut from the film.

EXAMPLE 6

| | |
|---|---|
| Trans-1a, 2, 3, 4a, 5, 6-hexahydro-9-hydroxy-4-n-propyl-4H—naphth[1,2-b]-1,4-oxazine hydrochloride | 0.1 mg. |
| Hydroxypropylmethyl cellulose q.s. ad. | 10 mg. |

Ophthalmic inserts are manufactured from compression molded films which are prepared on a Carver Press by subjecting the powdered mixture of the above ingredients to a compressional force of 12,000 lbs. (gauge) at 350° F. for one minute. The film is cooled under pressure by having cold water circulate in the platen. Ophthalmic inserts are then individually cut from the film with a punch. Each insert is placed into a vial, which is then placed in a humidity cabinet (88% R. H. at 30° C.) for two to four days. After removal from the humidity cabinet, the vials are stoppered and then capped. The vials containing the hydrated insert are then autoclaved at 250° F. for one-half hour.

It is highly preferred that the solid inserts of this invention are available for use by the patient in a pathogen free condition. Thus, it is preferred to sterilize the inserts and so as insure against recontamination, the sterilization is preferably conducted after packaging. The best mode of sterilizing is to employ ionizing irradiation including irradiation emanating from Cobalt 60 or high energy electron beams.

The drops, heretofore described in Example 1, are used in the usual way employing one to two drops per eye per patient per day. When inserts are employed usually one insert per patient per eye per day is satisfactory. Elevated intraocular pressure is a condition that must be carefully monitored on an individual basis. Thus an intraocular pressure lowering amount can be as little as 0.001–0.01 mg to as much as 0.100–0.250 mg per eye per patient per day of active medicament. As the individual differences between patient drug response are encountered and as experience with the medicament increases and information accumulates because of a larger patient population being developed, the daily ocular dose for the median population group can be stated with greater statistical accuracy. It may well be found that only a few patients respond to the minimal dose, and then only for a transient period. Also only a few patients may require administration of the drug at the higher dosage ranges. The dose also may be divided for administration. Thus, the quantities set forth previously can be administered in a course of individual deliveries comprising 1–4 or more times per day.

The concentration of active drug in any formulation can vary within a wide range. Clearly, as a function of concentration, the desired dose of formulation will consequently vary for example from a single drop or insert or multiple drops or inserts or larger or smaller inserts.

What is claimed is:

1. A method of treating elevated intraocular pressure which comprises topically applying to an eye in need of such treatment an effective intraocular pressure lowering amount of a dopamine agonist of structural formula I or II:

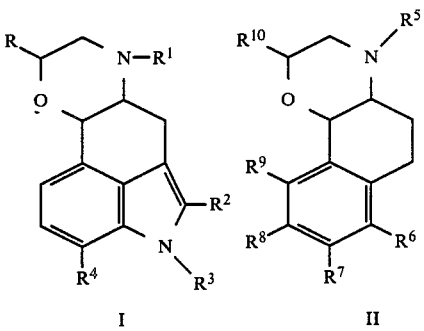

or an ophthalmologically acceptable salts thereof wherein:

R is
 (1) hydrogen,
 (2) $C_{1-6}$alkyl, or
 (3) phenyl;

$R^1$ is
 (1) hydrogen,
 (2) $C_{1-4}$alkyl,
 (3) $C_{3-6}$cycloalkyl,
 (4) $C_{3-6}$cycloaklyl-$C_{1-4}$alkyl,
 (5) $C_{3-4}$alkenyl,
 (6) phenyl-$C_{1-4}$alkyl;

$R^2$ is
 (1) hydrogen,
 (2) $C_{1-3}$alkyl,
 (3) chloro, or
 (4) bromo;

$R^3$ is
 (1) hydrogen,
 (2) $C_{1-3}$alkyl, or
 (3) phenyl-$C_{1-4}$alkyl;

$R^4$ is
 (1) hydrogen,
 (2) chloro,
 (3) bromo,
 (4) $C_{1-4}$alkoxy,
 (5) hydroxy, or
 (6) $C_{1-6}$alkyl, $R^5$ is
 (1) hydrogen,
 (2) $C_{1-4}$alkyl, (3) $C_{2-5}$alkenyl, or
(4) phenyl-$C_{1-4}$alkyl;

$R^6$, $R^7$, $R^8$, and $R^9$ are independently
(1) hydrogen,
(2) $C_{1-3}$alkoxy,
(3) hydroxy,
(4) $C_{1-4}$alkyl,
(5) halo,
(6) phenyl-$C_{1-3}$alkoxy, or
(7) adjacent R groups taken together are methylenedioxy; and $R^{10}$ is hydrogen, $C_{1-3}$alkyl or phenyl.

2. The method of claim 1, wherein $R^1$ is $C_{1-4}$alkyl, and $R^3$ is hydrogen.

3. The method of claim 2, wherein $R^2$, $R^3$ and $R^4$ are hydrogen.

4. The method of claim 3, wherein the compound is trans-4, 6, 6a, 8, 9, 10a-hexahydro-7-ethyl-7H-indolo[3,4:g,h][1,4]benzoxazine.

5. The method of claim 1, wherein $R^5$ is $C_{1-4}$alkyl, and one or more of $R^6$, $R^7$, $R^8$ and $R^9$ are hydroxy, methoxy, acetoxy or pivaloyloxy.

6. The method of claim 5 wherein $R^6$, $R^7$ and $R^8$ are hydrogen and $R^9$ is hydroxy, methoxy, acetoxy or pivaloyloxy.

7. The method of claim 7 wherein the compound is trans-1, 2, 3, 4a, 5, 6-hexahydro-9-hydroxy-4-n-propyl-4H-naphth[1,2-b]-1,4-oxazine.

* * * * *